US011622820B2

United States Patent
Cesa et al.

(10) Patent No.: US 11,622,820 B2
(45) Date of Patent: *Apr. 11, 2023

(54) SYSTEM AND METHOD FOR AN IMPROVED GRAPHICAL USER INTERFACE THAT PROVIDES INDEPENDENT CONTROL OF MULTIPLE RADIOFREQUENCY PROBES DURING AN ABLATION PROCEDURE

(71) Applicant: Avent, Inc., Alpharetta, GA (US)

(72) Inventors: Joseph A. Cesa, Franklin, MA (US); Lisa M. McGregor, Chamblee, GA (US); Jennifer J. Barrett, Alpharetta, GA (US); Tyler W. Crone, Atlanta, GA (US); Lee W. Rhein, Hollywood, FL (US); Christopher W. Thurrott, Townsend, MA (US); Morgan Rudolph, Nashua, NH (US); Scott Woodruff, Chicago, IL (US)

(73) Assignee: Avent, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/743,576

(22) Filed: May 13, 2022

(65) Prior Publication Data

US 2022/0338941 A1    Oct. 27, 2022

Related U.S. Application Data

(63) Continuation of application No. 16/416,361, filed on May 20, 2019, now Pat. No. 11,331,152.

(51) Int. Cl.
*A61B 34/00* (2016.01)
*G06F 3/0488* (2022.01)
(Continued)

(52) U.S. Cl.
CPC ............. *A61B 34/25* (2016.02); *A61B 5/743* (2013.01); *A61B 5/7435* (2013.01); *A61B 18/14* (2013.01);
(Continued)

(58) Field of Classification Search
CPC ....... A61B 34/25; A61B 5/743; A61B 5/7435; A61B 18/14; A61B 18/1482;
(Continued)

(56) References Cited

U.S. PATENT DOCUMENTS 7,574,257 B2 * 8/2009 Rittman, III ....... A61B 18/1477
607/2
8,348,934 B2 * 1/2013 Lorang ................. A61B 18/18
606/34

(Continued)

FOREIGN PATENT DOCUMENTS

WO    WO-2018116273 A1 *  6/2018

*Primary Examiner* — Yongjia Pan
(74) *Attorney, Agent, or Firm* — Meunier Carlin & Curfman LLC

(57) ABSTRACT

A system for delivering energy to a patient's body includes a plurality of probes, a touch-sensitive display screen, and a controller communicatively coupled to each of the probes and the display screen. The controller is configured to perform operations including displaying a plurality of dynamically sized channel control regions within a user interface of the touch-sensitive display screen. Each of the plurality of channel control regions corresponds with at least one of the plurality of probes and is sized based at least in part on a number of the plurality of probes. The operations can include detecting a user touch action directed to a user-selected channel control region of the plurality of dynamically sized channel control regions. The operations can include performing a control action associated with the (Continued)

probe(s) that correspond with the user-selected channel control region when the user touch action is detected.

20 Claims, 11 Drawing Sheets

(51) Int. Cl.
    *A61B 5/00*         (2006.01)
    *A61B 18/14*       (2006.01)
    *G06F 3/04845*    (2022.01)
    *G06F 3/04847*    (2022.01)
    *G06F 3/04886*    (2022.01)
    *A61B 17/00*      (2006.01)
    *A61B 18/00*      (2006.01)

(52) U.S. Cl.
    CPC ...... *A61B 18/1482* (2013.01); *G06F 3/04845* (2013.01); *G06F 3/04847* (2013.01); *G06F 3/04886* (2013.01); *A61B 2017/00199* (2013.01); *A61B 2018/00077* (2013.01); *A61B 2018/00083* (2013.01); *A61B 2018/00577* (2013.01); *G06F 2203/04803* (2013.01)

(58) Field of Classification Search
    CPC ........... A61B 2018/00077; A61B 2018/00083; A61B 2017/00199; A61B 2018/00577; A61B 2018/124; A61B 18/12; G06F 3/04845; G06F 3/04847; G06F 3/04886; G06F 2203/04803; G06F 3/0488
    See application file for complete search history.

(56) References Cited

U.S. PATENT DOCUMENTS

| | | | | |
|---|---|---|---|---|
| 10,420,480 | B1* | 9/2019 | Schermerhorn | A61B 5/389 |
| 2010/0250209 | A1* | 9/2010 | Pearson | A61B 18/1206 |
| | | | | 703/2 |
| 2015/0230749 | A1* | 8/2015 | Gharib | A61B 17/0218 |
| | | | | 600/546 |
| 2015/0297282 | A1* | 10/2015 | Cadouri | A61B 18/1492 |
| | | | | 606/34 |
| 2020/0078083 | A1* | 3/2020 | Sprinkle | A61B 18/14 |
| 2020/0085531 | A1* | 3/2020 | Harrison | A61B 90/90 |
| 2020/0197070 | A1* | 6/2020 | Dastjerdi | A61B 18/1206 |

\* cited by examiner

SYSTEM AND METHOD FOR AN IMPROVED GRAPHICAL USER INTERFACE THAT PROVIDES INDEPENDENT CONTROL OF MULTIPLE RADIOFREQUENCY PROBES DURING AN ABLATION PROCEDURE

CROSS-REFERENCE TO RELATED APPLICATIONS

This application is a continuation of U.S. patent application Ser. No. 16/416,361, filed May 20, 2019, which is incorporated herein by reference in its entirety.

BACKGROUND

The present disclosure relates generally to a system and method for applying energy for the treatment of tissue, and more particularly to a system and method for an improved graphical user interface that provides independent control of multiple radiofrequency probes during an ablation procedure.

Lower back injuries and chronic back pain are a major health problem resulting not only in a debilitating condition for the patient, but also in the consumption of a large proportion of funds allocated for health care, social assistance, and disability programs. Disc abnormalities and pain may result from trauma, repetitive use in the workplace, metabolic disorders, inherited proclivity, or aging. The existence of adjacent nerve structures and innervation of the disc are very important issues with respect to patient treatment for back pain.

A minimally invasive technique of delivering high-frequency electrical current has been shown to relieve localized pain in many patients. Generally, the high-frequency current used for such procedures is in the radio frequency (RF) range, i.e. between 100 kHz and 1 GHz and more specifically between 300-600 kHz. The RF electrical current is typically delivered from a generator via a plurality of connected electrodes that are placed in a patient's body, in a region of tissue that contains a neural structure suspected of transmitting pain signals to the brain. The electrodes generally include an insulated shaft with an exposed conductive tip to deliver the radio frequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations.

To extend the size of a lesion, radiofrequency treatment may be applied in conjunction with a cooling mechanism, whereby a cooling means is used to reduce the temperature of the tissue near an energy delivery device, allowing a higher voltage to be applied without causing an unwanted increase in local tissue temperature. The application of a higher voltage allows regions of tissue further away from the energy delivery device to reach a temperature at which a lesion can form, thus increasing the size/volume of the lesion.

Such procedures can be done using any suitable number of probes (e.g., from one probe up to four probes) or more, at a time. If one of the probes encounters a condition that causes the probe to stop during its procedure, however, the probe remains inactive until all remaining probes have completed their procedures. Once the other probes have completed their procedures, a user can troubleshoot the problem probe and restart the problem probe's procedure. Unfortunately, such workflow requires the user to waste valuable time waiting for procedures to finish, adding probe procedure times together, which extends the overall time that the patient must endure the treatment procedure.

A graphical user interface can be provided on a display screen to allow the user to control the various procedures. However, the size of the graphical user interface is practically limited by the size of the display screen. Additionally, the number of connected or active probes can vary (e.g., from one probe to four probes, or more) over time in a given application and/or between different applications (e.g., depending on patient-specific circumstances). Current graphical user interfaces lack flexibility and/or adaptability such variations in the number of probes. As such, existing graphical user interfaces may fail to provide the user with the ability to quickly, accurately, and/or independently control the various treatment procedures performed by the various probes.

Thus, the present disclosure is directed to systems and methods for an improved graphical user interface that provides independent control of multiple radiofrequency probes during an ablation procedure.

SUMMARY

Objects and advantages of the system and methods described herein will be set forth in part in the following description, or may be obvious from the description, or may be learned through practice of the described system and methods.

One implementation of the present disclosure is a system for delivering energy to a patient's body. The system includes a plurality of probes each having an elongate member with a distal region having an electrically non-conductive outer circumferential portion and a proximal region. Each of the plurality of probes further includes an electrically conductive energy delivery device extending distally from the electrically non-conductive outer circumferential portion for delivering one of electrical and radiofrequency energy to the patient's body. The energy delivery devices further include an electrically conductive outer circumferential surface. The system also includes a touch-sensitive display screen and at least one controller communicatively coupled to each of the plurality of probes and the touch-sensitive display screen. The controller includes memory and a processor, and, the memory stores instructions that, when executed by the processor, cause the processor to perform operations. The operations include displaying a plurality of dynamically sized channel control regions within a user interface of the touch-sensitive display screen. Each of the plurality of dynamically sized channel control regions correspond with at least one of the plurality of probes. The plurality of dynamically sized channel control regions are sized based at least in part on a number of the plurality of probes. The operations include detecting a user touch action directed to a user-selected channel control region of the plurality of dynamically sized channel control regions of the user interface. The operations include performing a control action associated with the at least one probe that corresponds with the user-selected channel control region of the plurality of dynamically sized channel control regions when the user touch action is detected.

In a particular embodiment, the controller is further configured to resize the plurality of dynamically sized channel control regions in response to an additional probe being communicatively coupled with the controller. In a particular embodiment, the controller is further configured to resize the plurality of dynamically sized channel control regions in response to the user touch action when the user touch action requests that the user-selected channel control region be hidden from the user interface. In a particular embodiment, the controller is further configured to resize the plurality of dynamically sized channel control regions in response to completed performance of a treatment procedure of at least one of the plurality of probes.

In a particular embodiment, the controller is further configured to monitor a status of a treatment procedure associated with at least one of the plurality of probes. The controller is further configured to display a status notification indicative of the status within the dynamically sized channel control region that corresponds with the at least one of the plurality of probes.

In some embodiments, the controller can be further configured to display a virtual control object within at least one of the plurality of dynamically sized channel control regions. For example, the virtual control object can include at least one of a start button, a restart button, a reset button, a stop button, or an individual parameter control button. As another example, the virtual control object can include an individual parameter control button and performing the control action includes adjusting an individual parameter setting associated with a treatment procedure of the at least one probe that corresponds with the user-selected channel control region when the user touch action is directed to the individual parameter control button. For instance, the individual parameter setting can include at least one of a temperature setting or an individual duration time associated with the treatment procedure of the at least one probe that corresponds with the user-selected channel control region. As yet another example, the virtual control object can include a slider bar, and the controller can be configured to initiate a treatment procedure with the at least one probe that corresponds with the user-selected channel control region when the user touch action is directed to the slider bar.

Another implementation of the present disclosure is a method of treating tissue of a patient's body is provided. The method includes communicatively coupling a controller to the probe assembly. The controller is communicatively coupled to a touch-sensitive display screen. The method includes inserting the plurality of probes into the patient's body adjacent the tissue of the patient's body. The method includes displaying a plurality of dynamically sized channel control regions within a user interface of the touch-sensitive display screen. Each of the plurality of dynamically sized channel control regions correspond with at least one of the plurality of probes. The plurality of dynamically sized channel control regions are sized based at least in part on a number of the plurality of probes. The method includes detecting a user touch action directed to a user-selected channel control region of the plurality of dynamically sized channel control regions of the user interface. The method includes performing a control action associated with the at least one probe that corresponds with the user-selected channel control region of the plurality of dynamically sized channel control regions.

In a particular embodiment, the method includes resizing the plurality of dynamically sized channel control regions in response to an additional probe being communicatively coupled with the controller. In a particular embodiment, the method includes resizing the plurality of dynamically sized channel control regions in response to the user touch action when the user touch action requests that the user-selected channel control region be hidden from the user interface. In a particular embodiment, the method includes resizing the plurality of dynamically sized channel control regions in response to completed performance of a treatment procedure of at least one of the plurality of probes.

In a particular embodiment, the method includes monitoring a status of a treatment procedure associated with at least one of the plurality of probes and displaying a status notification indicative of the status within the dynamically sized channel control region that corresponds with the at least one of the plurality of probes.

In some embodiments, the method can include displaying a virtual control object within at least one of the plurality of dynamically sized channel control regions. For example, the virtual control object can include at least one of a start button, a restart button, a reset button, or a stop button. As another example, the virtual control object can include an individual parameter control button, and performing the control action includes adjusting an individual parameter setting associated with a treatment procedure of the at least one probe that corresponds with the user-selected channel control region. For instance, the individual parameter setting can include at least one of a temperature setting or an individual duration time associated with the treatment procedure of the at least one probe that corresponds with the user-selected channel control region. As yet another example, the virtual control object can include a slider bar, and the method can include initiating, resetting, or restarting a treatment procedure with the at least one probe that corresponds with the user-selected channel control region when the user touch action is directed to the slider bar.

In a particular embodiment, the method can include displaying at least one real-time operating parameter of the treatment procedure of the at least one probe within the dynamically sized channel control region that corresponds with the at least one probe. The one or more real-time operating parameters can include at least one of an actual temperature, an impedance, an actual time, a run time, a power output of the energy delivery device, a threshold temperature, or a combination thereof.

Yet another implementation of the present disclosure is a system for delivering energy to a patient's body is provided. The system includes a plurality of probes configured to delivering at least one of electrical or radiofrequency energy to a patient's body. The system includes a controller communicatively coupled to each of the plurality of probes and configured to control a respective flow of electrical current to each of the plurality of probes. The system includes a touch-sensitive display screen and a controller communicatively coupled to each of the plurality of probes and the touch-sensitive display screen. The controller is configured to control a respective flow of electrical current to each of the plurality of probes. The controller includes memory and a processor. The memory storing instructions that, when executed by the processor, cause the processor to perform operations. The operations include displaying a plurality of dynamically sized channel control regions within a user interface of the touch-sensitive display screen. Each of the plurality of dynamically sized channel control regions correspond with at least one of the plurality of probes. The plurality of dynamically sized channel control regions are sized based at least in part on a number of the plurality of probes. The operations include monitoring a status of a treatment procedure associated with the at least one of the plurality of probes; displaying a status notification indicative of the status within the dynamically sized channel control region that corresponds with the at least one of the plurality of probes; detecting a user touch action directed to a user-selected channel control region of the plurality of dynamically sized channel control regions of the user interface; and when the user touch action is detected, performing a control action associated with the probe that corresponds with the user-selected channel control region of the plurality of dynamically sized channel control regions.

These and other features, aspects and advantages will become better understood with reference to the following description and appended claims. The accompanying drawings, which are incorporated in and constitute a part of this specification, illustrate embodiments of the present disclosure and, together with the description, explain the principles of the present disclosure.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Figure 1A:
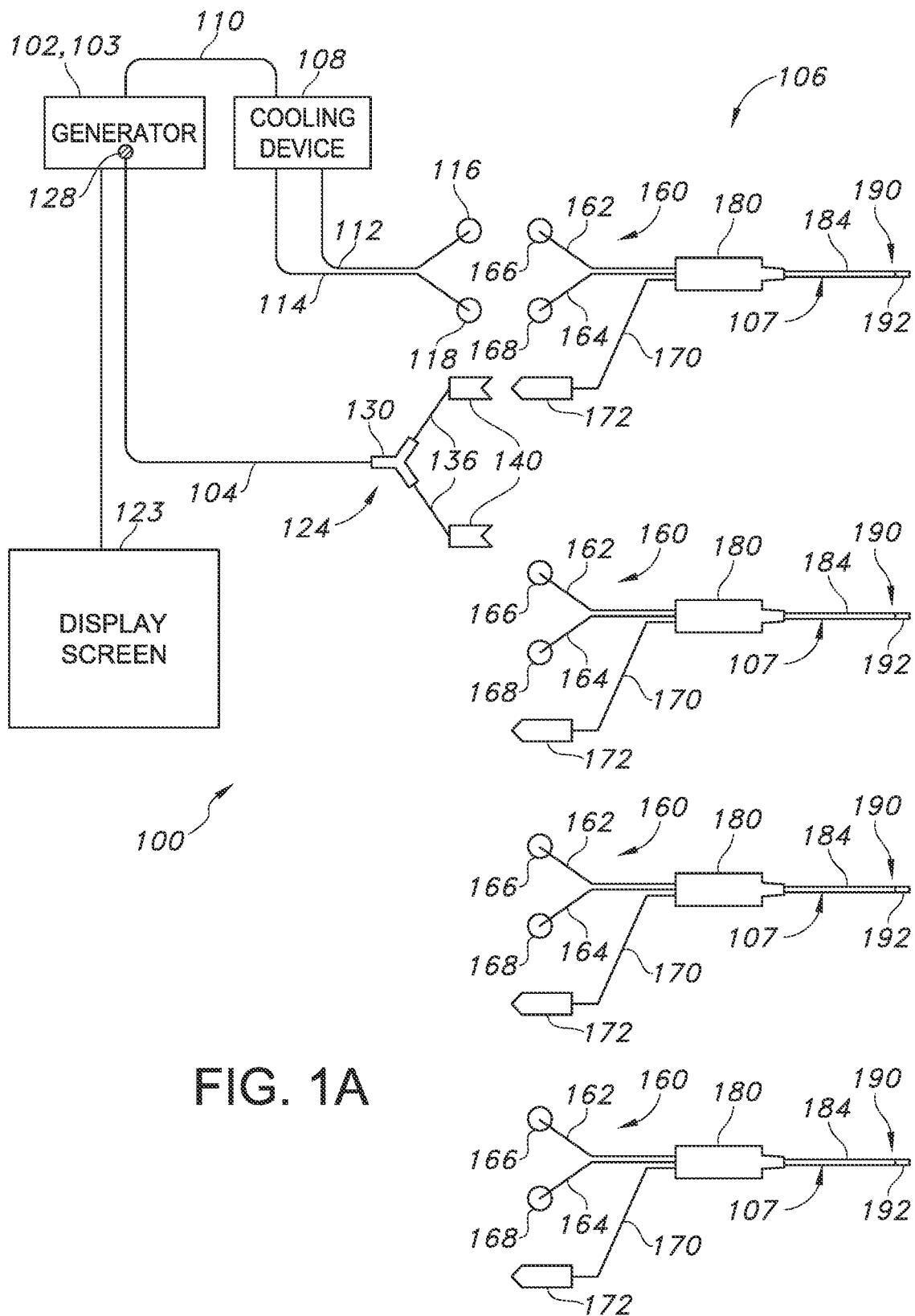
FIG. 1A illustrates a portion of one embodiment of a system for applying radio frequency electrical energy to a patient's body, according to some embodiments.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to any effect achieved through the application of energy to a tissue in a patient's body, and the invention is not intended to be limited in this regard. Furthermore, for the purposes of this description, proximal generally indicates that portion of a device or system next to or nearer to a user (when the device is in use), while the term distal generally indicates a portion further away from the user (when the device is in use).

According to one aspect of the present disclosure, a controller can be communicatively to a plurality of probes and a touch-sensitive display screen. The controller can be configured to perform various operations associated with receiving user input and controlling aspects of treatment procedures performed with the probes. For example, in one embodiment, the controller can be configured to display a plurality of dynamically sized channel control regions within a user interface of the touch-sensitive display screen. Each channel control region can correspond with a one or more of the probes. Individual controls and/or data associated with each probe's treatment procedure can be provided within each respective channel control region.

The channel control regions can be dynamically sized based at least in part on a number of the plurality of probes communicatively coupled with the controller. For example, when additional probes are communicatively coupled with the controller, the existing channel control regions can be reduced in size and an additional channel control region can be displayed corresponding to the additional probe. As such, the user interface may provide the user with individual controls for each probe that is currently communicatively coupled with the controller in a space-efficient manner.

As another example, when a treatment procedure of one probe has been completed, the user can hide the corresponding channel control region. The remaining channel control regions may be resized to be larger, providing better access to the controls for the remaining channel control regions. Alternatively, the controller can provide the user with the ability to reset or restart the treatment procedure of the completed probe.

Aspects of the present disclosure can provide the user with a versatile and adaptable user interface that facilitates individual control and/or provides individual feedback associated with the respective treatment procedures being performed with the probes. More specifically, the dynamically sized channel control regions can provide the user with access to important controls while also reducing visual clutter. As a result, the user may more quickly identify and correct issues, for example, before such issues result in a stoppage or delay of one or more of the treatment procedures.

Additionally, aspects of the present disclosure provide the user with the ability to reset and/or restart individual treatment procedures. For example, if a probe experiences unsatisfactory operating conditions, and the associated treatment procedure is terminated, the remaining probes may be unaffected and may continue performing the treatment procedures. The user interface can allow the user to restart the stopped treatment procedure without stopping or otherwise impairing the progress of the other treatment procedures. Additionally, if the user detects a problem with one of the treatment procedures (e.g., based on information displayed within the user interface) and would like to stop the treatment procedure, the user can do so without stopping the remaining treatment procedures. The controller can be configured to independently control aspects of each treatment procedure, for example using independent control loops, to facilitate such independent stopping and starting of the treatment procedures.

Referring now to the drawings, FIG. 1A illustrates a schematic diagram of one embodiment of a system 100 of the present invention. As shown, the system 100 includes a generator 102, a cable 104, at least one probe assembly 106 having a plurality of probes 107, one or more cooling devices 108, a pump cable 110, one or more proximal cooling supply tubes 112 and one or more proximal cooling return tubes 114. As shown in the illustrated embodiment, the generator 102 is a radio frequency (RF) generator but may optionally be any energy source that may deliver other forms of energy, including but not limited to microwave energy, thermal energy, ultrasound, and optical energy. The generator 102 may include or be communicatively coupled with a controller 103 that is operable to communicate with one more devices, for example with the probes 107 and the one or more cooling devices 108. Such communication may be unidirectional or bidirectional depending on the devices used and the procedure performed.

The controller 103 may correspond to any suitable processor-based device(s), such as a computing device or any combination of computing devices. Thus, in several embodiments, the controller 103 may include one or more processor(s) and associated memory device(s) configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) of the controller 103 may generally comprise memory element(s) including, but not limited to, computer readable medium (e.g., random access memory (RAM)), computer readable non-volatile medium (e.g., a flash memory), a compact disc-read only memory (CD-ROM), a magneto-optical disk (MOD), a digital versatile disc (DVD) and/or other suitable memory elements. Such memory device(s) may generally be configured to store suitable computer-readable instructions that, when implemented by the processor(s) configure the controller 103 to perform various computer-implemented functions, such as one or more aspects of the method 1000 described below with reference to FIG. 10.

In addition, as shown, a distal region 124 of the cable 104 may include a splitter 130 that divides the cable 104 into two distal ends 136 such that the probes 107 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two distal ends 136 of the cable 104 terminate in connectors 140 operable to couple to the probes 107 and establish an electrical connection between the probes 107 and the generator 102. In alternate embodiments, the system 100 may include a separate cable for each probe assembly 106 being used to couple the probes 107 to the generator 102. Alternatively, the splitter 130 may include more than two distal ends. Such a connector is useful in embodiments having more than two devices connected to the generator 102, for example, if more than two probe assemblies are being used.

Figure 1B:
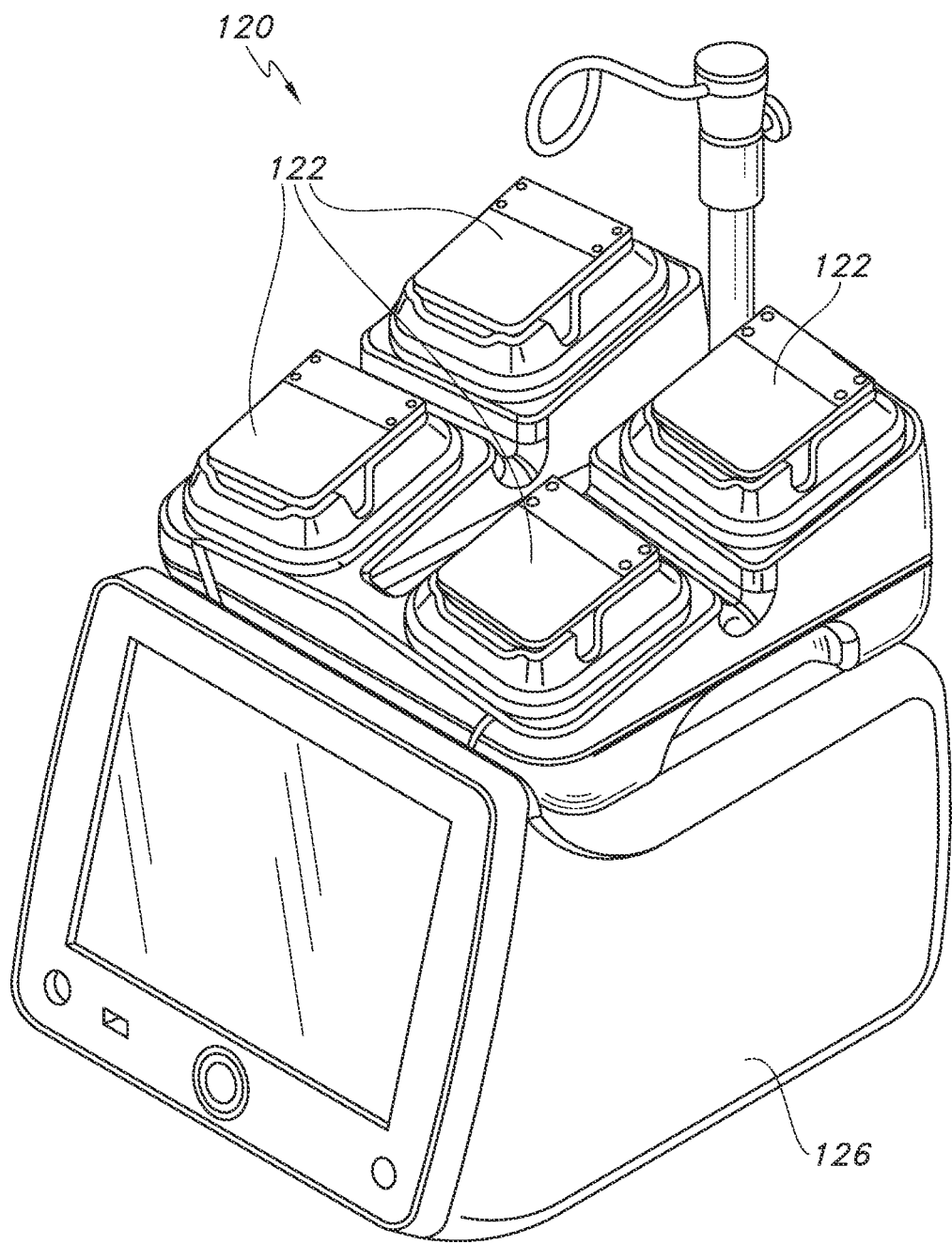
FIG. 1B illustrates a perspective view of one embodiment of a pump assembly, according to some embodiments.

The cooling device(s) 108 may include any means of reducing a temperature of material located at and proximate to one or more of the probes 107. For example, as shown in FIG. 1B, the cooling devices 108 may include a pump assembly 120 having one or more peristaltic pumps 122 operable to circulate a fluid from the cooling devices 108 through one or more proximal cooling supply tubes 112, the probes 107, one or more proximal cooling return tubes 114 and back to the one or more cooling devices 108. For example, as shown, the pump assembly 120 includes four peristaltic pumps 122 coupled to a power supply 126. In alternate embodiments, the pump assembly 120 may include only one peristaltic pump or greater than four pumps. The fluid may be water or any other suitable fluid.

Referring to FIG. 1A, the controller 103 may be communicatively coupled with a display screen d (e.g., a touch-sensitive display screen) for displaying a user interface, for example as described below with reference to FIGS. 4 through 9D. The user interface may display various aspects of a treatment procedure, including but not limited to any operating parameters that are relevant to a treatment procedure, such as temperature, impedance, etc. and errors or warnings related to a treatment procedure. The display screen 123 may be responsive to user touch actions directed to the user interface such that the user can adjust one or more individual operating parameters of the various treatment procedures.

The controller 103 may be configured for facilitating communication between the cooling devices 108 and the generator 102. In this way, feedback control is established between the cooling device(s) 108 and the generator 102. The feedback control may include the generator 102, the probes 107 and the cooling devices 108, although any feedback between any two devices is within the scope of the present invention. The feedback control may be implemented, for example, in a control module which may be a component of the generator 102. In such embodiments, the generator 102 is operable to communicate bi-directionally with the probes 107 as well as with the cooling devices 108. In the context of this invention, bi-directional communication refers to the capability of a device to both receive a signal from and send a signal to another device.

As an example, the controller 103 may receive temperature measurements from one or more of the plurality of probes 107. Based on the temperature measurements, the generator 102 may perform some action, such as modulating the power that is sent to the probes 107 (e.g., using one or more control loops). More specifically, aspects of the treatment procedures performed by the various probes 107 may be actively controlled, for example using a control loop (e.g., proportional-integral, or proportional-integral-derivative control loop) based on information received by one or more sensors. For example, an amount of energy delivered through the energy delivery devices 192 may be controlled. The flow rate of the peristaltic pumps 122 and resulting cooling may also be actively controlled. In further embodiments, the generator 102 may control the energy delivered to the tissue based on the measured temperature measured by the temperature sensing element(s) 402 (see FIG. 2) and/or impedance sensors. For example, power to each of the probes 107 can be increased when a temperature measurement is low or decreased when a measurement is high. This variation of power may be different for each probe assembly. In some cases, the generator 102 may terminate power to one or more probes 107. Thus, the generator 102 may receive a signal (e.g., temperature measurement) from one or more of probes 107, determine the appropriate action, and send a signal (e.g., decreased or increased power) back to one or more of the probes 107. Alternatively, the generator 102 may send a signal to the cooling devices 108 to either increase or decrease the flow rate or degree of cooling being supplied to one or more of the probes 107.

More specifically, the pumps may communicate a fluid flow rate to the controller 103 and may receive communications from the controller 103 instructing the pumps to modulate this flow rate. In some instances, the peristaltic pumps may respond to the controller 103 by changing the flow rate or turning off for a period of time. With the cooling devices 108 turned off, any temperature sensing elements associated with the probes 107 would not be affected by the cooling fluid allowing a more precise determination of the surrounding tissue temperature to be made. In addition, when using more than one probe assembly 106, the average temperature or a maximum temperature in the temperature sensing elements associated with probes 107 may be used to modulate cooling.

In other embodiments, the cooling devices 108 may reduce the rate of cooling or disengage depending on the distance between the probes 107. For example, when the distance is small enough such that a sufficient current density exists in the region to achieve a desired temperature, little or no cooling may be required. In such an embodiment, energy is preferentially concentrated between the energy delivery devices 192 through a region of tissue to be treated, thereby creating a strip lesion. A strip lesion is characterized by an oblong volume of heated tissue that is formed when an active electrode is near a return electrode of similar dimensions. This occurs because at a given power, the current density is preferentially concentrated between the electrodes and a rise in temperature results from current density.

The cooling devices 108 may also communicate with the controller 103 to alert the controller 103 to one or more possible errors and/or anomalies associated with the cooling devices 108. For example, if cooling flow is impeded or if a lid of one or more of the cooling devices 108 is opened. The controller 103 may then act on the error signal by at least one of alerting a user, aborting the procedure, and modifying an action.

Still referring to FIG. 1A, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114. In one embodiment, the proximal supply tube connectors 116 are female luer-lock type connectors and the proximal return tube connectors 118 are male luer-lock type connectors although other connector types are intended to be within the scope of the present invention.

In addition, as shown in FIG. 1A, each of the probes 107 may include a proximal region 160, a handle 180, a hollow elongate shaft 184, and a distal tip region 190 that includes the one or more energy delivery devices 192. Further, as shown, the proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probes 107, but alternate embodiments with rigid tubes are possible.

Further, in several embodiments, the distal supply tube connector 166 may be a male luer-lock type connector and the distal return tube connector 168 may be a female luer-lock type connector. Thus, the proximal supply tube connector 116 may be operable to interlock with the distal supply tube connector 166 and the proximal return tube connector 118 may be operable to interlock with the distal return tube connector 168.

The probe cable connector 172 may be located at a proximal end of the probe assembly cable 170 and may be operable to reversibly couple to one of the connectors 140, thus establishing an electrical connection between the controller 103 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the controller 103 to the one or more energy delivery devices 192 as well as to connect multiple temperature sensing devices to the controller 103 as discussed below.

The energy delivery devices 192 may include any means of delivering energy to a region of tissue adjacent to the distal tip region 190. For example, the energy delivery devices 192 may include an ultrasonic device, an electrode or any other energy delivery means and the invention is not limited in this regard. Similarly, energy delivered via the energy delivery devices 192 may take several forms including but not limited to thermal energy, ultrasonic energy, radiofrequency energy, microwave energy or any other form of energy. For example, in one embodiment, the energy delivery devices 192 may include an electrode. The active region of the electrode may be 2 to 20 millimeters (mm) in length and energy delivered by the electrode is electrical energy in the form of current in the RF range. The size of the active region of the electrode can be optimized for placement within an intervertebral disc, however, different sizes of active regions, all of which are within the scope of the present invention, may be used depending on the specific procedure being performed. In some embodiments, feedback from the controller 103 may automatically adjust the exposed area of the energy delivery device 192 in response to a given measurement such as impedance or temperature. For example, in one embodiment, the energy delivery devices 192 may maximize energy delivered to the tissue by implementing at least one additional feedback control, such as a rising impedance value.

Figure 2:
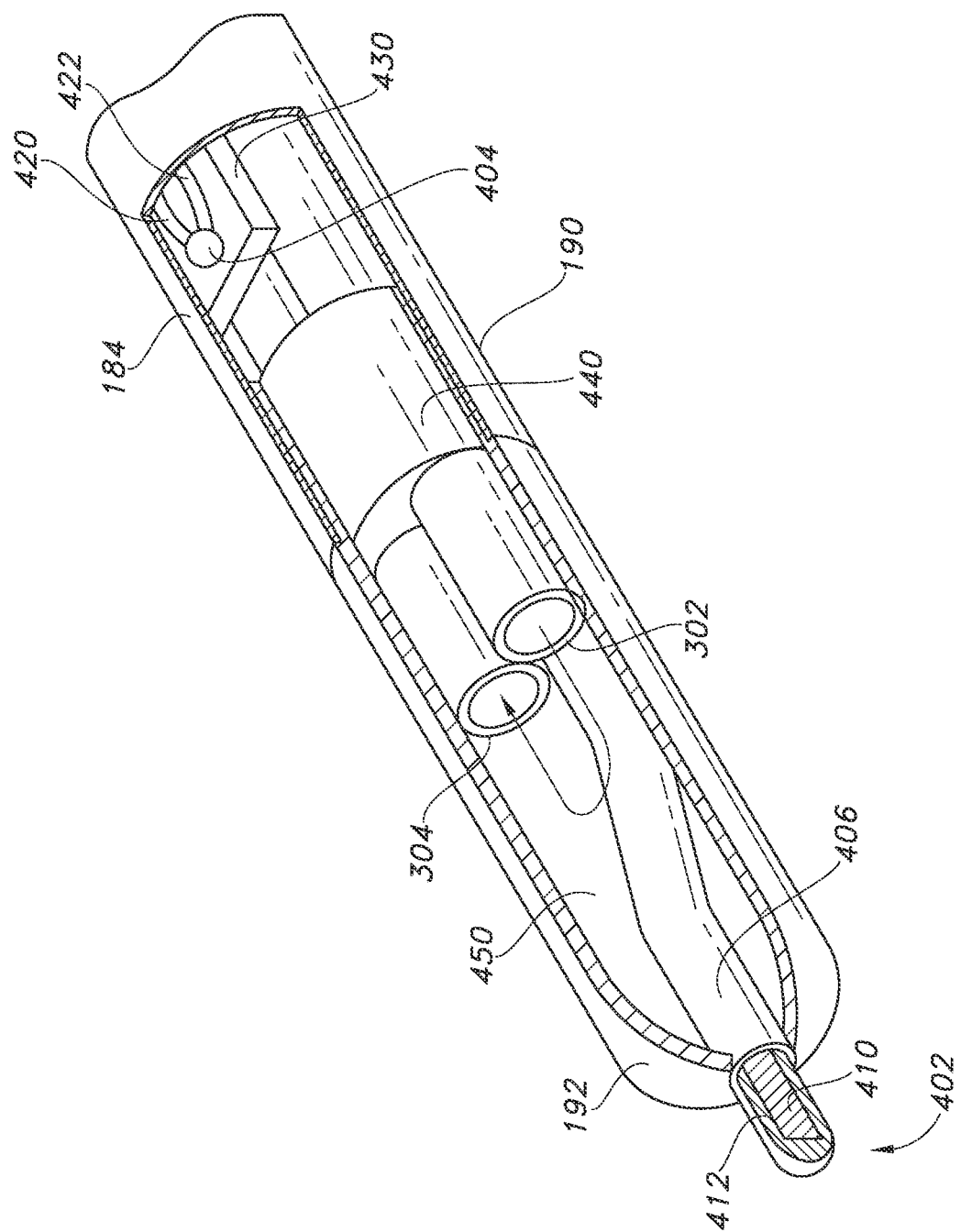
FIG. 2 illustrates a perspective cut-away view of one embodiment of a distal tip region of a probe assembly, according to some embodiments.

Referring in detail to FIG. 2, a perspective cut-away view of one embodiment of the distal tip region 190 of the probe assembly 106 is illustrated. As shown, the distal tip region 190 includes one or more temperature sensing elements 402 which are operable to measure the temperature at and proximate to the one or more energy delivery devices 192. The temperature sensing elements 402 may include one or more thermocouples, thermometers, thermistors, optical fluorescent sensors, or any other means of sensing temperature. In one embodiment, the temperature sensing elements 402 are connected to the controller 103 via probe assembly cable 170 and cable 104 although any means of communication between the temperature sensing elements 402 and the controller 103, including wireless protocols, are included within the scope of the present invention. More specifically, as shown, the temperature sensing element(s) 402 may include a thermocouple junction made by joining a stainless steel hypotube 406 to a constantan wire 410, wherein the constantan wire 410 is insulated by insulation 412. In this embodiment, the junction of hypotube 406 and the constantan wire 410 is made by laser welding, although any other means of joining two metals may be used. Furthermore, in this embodiment, the hypotube 406 and the constantan wire 410 extend through a lumen of the elongate shaft 184 and connect to the probe assembly cable 170 within the handle 180.

Further, as shown, the temperature sensing element 402 of each probe 107 protrudes beyond the energy delivery device 192. Placing the temperature sensing elements 402 at this location, rather than within a lumen 450 defined by the energy delivery device 192, is beneficial because it allows the temperature sensing element 402 to provide a more accurate indication of the temperature of tissue proximate to the energy delivery device 192. This is due to the fact that, when extended beyond the energy delivery device 192, the temperature sensing element 402 will not be as affected by the cooling fluid flowing within the lumen 450 as it would be were it located within lumen 450. Thus, in such embodiments, the probe assembly 106 includes a protrusion protruding from the distal region of the probe assembly, whereby the protrusion is a component of the temperature sensing element 402.

Referring still to FIG. 2, the probe assembly 106 may further include one or more secondary temperature sensing elements 404 located within the elongate shaft 184 at some distance away from the energy delivery device 192, and positioned adjacent a wall of the elongate shaft 184. The secondary temperature sensing elements 404 may similarly include one or more thermocouples, thermometers, thermistors, optical fluorescent sensors, or any other means of sensing temperature. For example, as shown, the secondary temperature sensing element 404 is a thermocouple made by joining copper and constantan thermocouple wires, designated as 420 and 422, respectively. Further, in certain embodiments, the copper and constantan wires 420 and 422 may extend through a lumen of the elongate shaft 184 and may connect to the probe assembly cable 170 within the handle 180.

In addition, the probe assembly 106 may further include a thermal insulator 430 located proximate to any of the temperature sensing elements 402, 404. As such, the thermal insulator 430 may be made from any thermally insulating material, for example silicone, and may be used to insulate any temperature sensing element from other components of the probe assembly 106, so that the temperature sensing element will be able to more accurately measure the temperature of the surrounding tissue. More specifically, as shown, the thermal insulator 430 is used to insulate the temperature sensing element 404 from cooling fluid passing through the shaft supply tube 302 and the shaft return tube 304.

In further embodiments, the probe assembly 106 may also include a radiopaque marker 440 incorporated somewhere along the elongate shaft 184. For example, as shown in FIG. 2, an optimal location for a radiopaque marker may be at or proximate to the distal tip region 190, adjacent the energy delivery device 192. The radiopaque markers are visible on fluoroscopic x-ray images and can be used as visual aids when attempting to place devices accurately within a patient's body. These markers can be made of many different materials, as long as they possess sufficient radiopacity. Suitable materials include, but are not limited to silver, gold, platinum, and other high-density metals as well as radiopaque polymeric compounds. Various methods for incorporating radiopaque markers into or onto medical devices may be used, and the present invention is not limited in this regard.

Further, as shown, the elongate shaft 184 and the electrode 192 overlap to secure the electrode in place. In this embodiment, the lumen defined by the elongate shaft 184 and the electrode 192 at this portion of the distal tip region 190 contains a radiopaque marker 440 made of silver solder, which fills the lumen such that any cooling fluid supplied to the probe assembly 106, that is not located within one of the cooling tubes described earlier, is confined to the distal tip region 190 of probe assembly 106. Thus, in such an embodiment, the silver solder may be referred to as a flow impeding structure since it functions to restrict the circulation of fluid to a specific portion (in this case, at least a portion of distal region 190) of the probe assembly 106.

In other words, cooling fluid may flow from the cooling devices 108, through the cooling supply tubes to the distal tip region 190 of the probe assembly 106. The cooling fluid may then circulate within the lumen 450 defined by the electrode 192 to provide cooling thereto. As such, the internally-cooled probe as described herein is defined as a probe having such a configuration, whereby a cooling medium does not exit probe assembly 106 from a distal region of probe assembly 106. The cooling fluid may not circulate further down the elongate shaft 184 due to the presence of the silver solder, and flows through the cooling return tubes back to the cooling devices 108. In alternate embodiments, other materials may be used instead of silver solder, and the invention is not limited in this regard. As described above, providing cooling to the probes 107 allows heat delivered through the energy delivery devices 192 to be translated further into the tissue without raising the temperature of the tissue immediately adjacent the energy delivery device 192.

As mentioned above, the system 100 of the present invention may further include one or more introducer tubes. Generally, introducer tubes may include a proximal end, a distal end, and a longitudinal bore extending therebetween. Thus, the introducer tubes (when used) are operable to easily and securely couple with the probe assembly 106. For example, the proximal end of the introducer tubes may be fitted with a connector able to mate reversibly with handle 180 of probe assembly 106. An introducer tube may be used to gain access to a treatment site within a patient's body and a hollow elongate shaft 184 of a probe assembly 106 may be introduced to said treatment site through the longitudinal bore of said introducer tube. Introducer tubes may further include one or more depth markers to enable a user to determine the depth of the distal end of the introducer tube within a patient's body. Additionally, introducer tubes may include one or more radiopaque markers to ensure the correct placement of the introducers when using fluoroscopic guidance.

The system may also include one or more stylets. A stylet may have a beveled tip to facilitate insertion of the one or more introducer tubes into a patient's body. Various forms of stylets are well known in the art and the present invention is not limited to include only one specific form. Further, as described above with respect to the introducer tubes, the stylets may be operable to connect to a power source and may therefore form part of an electrical current impedance monitor. In other embodiments, one or more of the probe assemblies 106 may form part of an electrical current impedance monitor. Thus, the controller 103 may receive impedance measurements from one or more of the stylets, the introducer tubes, and/or the probes 107 and may perform an action, such as alerting a user to an incorrect placement of an energy delivery device 192, based on the impedance measurements.

Figure 3:
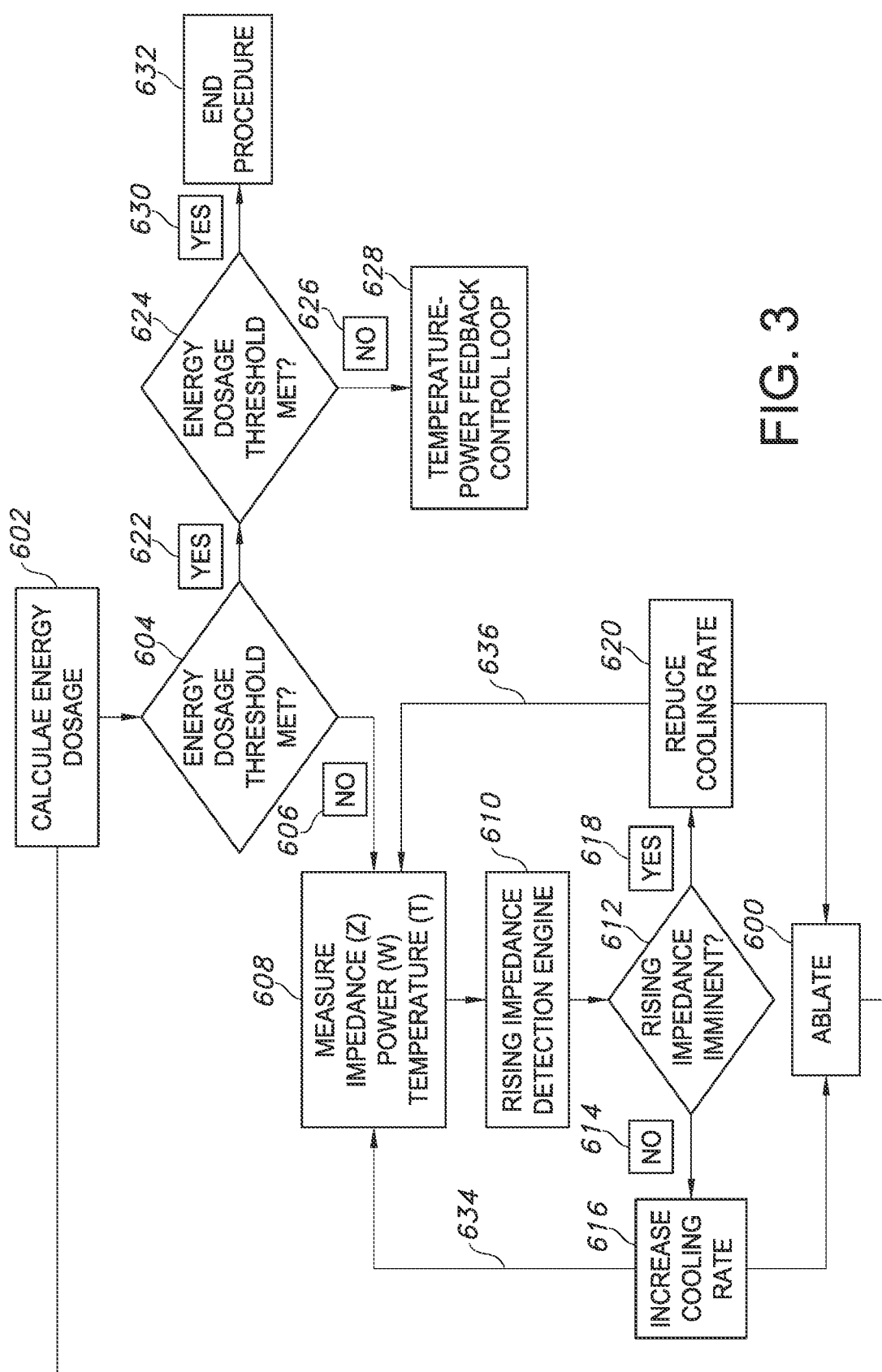
FIG. 3 illustrates a block diagram of one embodiment of a treatment procedure for actively controlling energy delivered to tissue in the patient's body by controlling an amount of energy delivered by the energy delivery devices and a flow rate of the pumps of the pump assembly, according to some embodiments.

FIG. 3 illustrates a block diagram of one embodiment of a control loop for controlling aspects of a treatment procedure. As shown at 600, ablation is initialized. As shown at 602, the energy dosage may be calculated using simple numerical integration techniques. As shown at 604, the calculated energy dosage may then be compared against a preset energy dosage threshold. If the dosage is not satisfied as shown at 606, the procedure continues to 608 to mitigate rising impedance of the internally-cooled probes 107 during the treatment procedure. More specifically, as shown, one or more procedure parameters are monitored while delivering the energy from the generator 102 to the tissue through the energy delivery devices 192. The procedure parameter(s) described herein may include, for example, a temperature of the tissue, an impedance of the tissue, a power demand of the energy delivery device 192, or similar, or combinations thereof. Further, as shown, the procedure parameter(s) 608 may be fed into a rising impedance detection engine 610. As shown at 612, the rising impedance detection engine 610 is configured to determine, e.g. in real-time, whether a rising impedance event is likely to occur in a predetermined time period (i.e. whether the rising impedance event is imminent) based on the received procedure parameter(s) 608. The rising impedance detection engine 610 can then determine a command for the pump assembly 120 based on whether the rising impedance event is likely to occur in the predetermined time period.

If not imminent, as shown at 614, the cooling rate can be increased, e.g. by increasing the pump speed (e.g. via the RPM controllers 125) of the peristaltic pumps 122 as shown at 616. After the cooling rate is increased, the ablation 600 continues. If a rising impedance event is imminent, as shown at 618, the cooling rate can be reduced, e.g. by decreasing the pump speed (e.g. via the RPM controllers 125) of the peristaltic pumps 122 as shown at 620. In other words, in several embodiments, the peristaltic pumps 122 may be independently controlled via their respective RPM controllers 125 to alter the rate of cooling to each electrode 192 of the probes 107. In such embodiments, the power supply 126 of the pump assembly 120 may be decoupled, at least in part, from the generator 102. Further, as shown, the system 550 operates using closed-loop feedback control 634, 636.

Once the energy dosage threshold is satisfied, as shown at 622, the treatment procedure is configured to check if the thermal dosage threshold has been satisfied as shown at 624. If the thermal dosage has not been satisfied, as shown at 626, the treatment procedure proceeds through the independent temperature-power feedback control loop as shown at 628. More specifically, in certain embodiments, the amount of energy delivered through the energy delivery device 192 may be controlled by defining a predetermined threshold temperature for treating the tissue, ramping up the temperature of the tissue via the generator 102 through the energy delivery device 192 to the predetermined threshold temperature, and maintaining the temperature of the tissue at the predetermined threshold temperature to create a lesion in the tissue. In such embodiments, the temperature of the tissue may be maintained at the predetermined threshold temperature as a function of at least one of a power ramp rate, an impedance level, an impedance ramp rate, and/or a ratio of impedance to power.

Only when the thermal dosage threshold has been satisfied, as shown at 630, the procedure terminates as shown at 632. Thus, the system and method of the present disclosure provides the unique features of probe(s) with inherently high-power demand (i.e. short thermocouple protrusion), a pump-modulated power algorithm, a preset energy dosage or total average power threshold, and/or a rising impedance detection engine 610.

Following treatment, energy delivery and cooling may be stopped and the probes 107 are removed from the introducers, where used. A fluid such as an antibiotic or contrast agent may be injected through the introducers, followed by removal of the introducers. Alternatively, the distal tips of the probes 107 may be sharp and sufficiently strong to pierce tissue so that introducers may not be required. As mentioned above, positioning the probes 107, and more specifically the energy delivery devices 192, within the patient's body, may be assisted by various means, including but not limited to fluoroscopic imaging, impedance monitoring and tactile feedback. Additionally, some embodiments of this method may include one or more steps of inserting or removing material into a patient's body.

A system of the present invention may be used in various medical procedures where usage of an energy delivery device may prove beneficial. Specifically, the system of the present invention is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

Using liquid-cooled probes 107 with an appropriate feedback control system as described herein also contributes to the uniformity of the treatment. The cooling distal tip regions 190 of the probes 107 helps to prevent excessively high temperatures in these regions which may lead to tissue adhering to the probes 107 as well as an increase in the impedance of tissue surrounding the distal tip regions 190 of the probes 107. Thus, by cooling the distal tip regions 190 of the probes 107, higher power can be delivered to tissue with a minimal risk of tissue charring at or immediately surrounding the distal tip regions 190. Delivering higher power to energy delivery devices 192 allows tissue further away from the energy delivery devices 192 to reach a temperature high enough to create a lesion and thus the lesion will not be limited to a region of tissue immediately surrounding the energy delivery devices 192 but will rather extend preferentially from a distal tip region 190 of one probe assembly 106 to the other.

Figure 4:
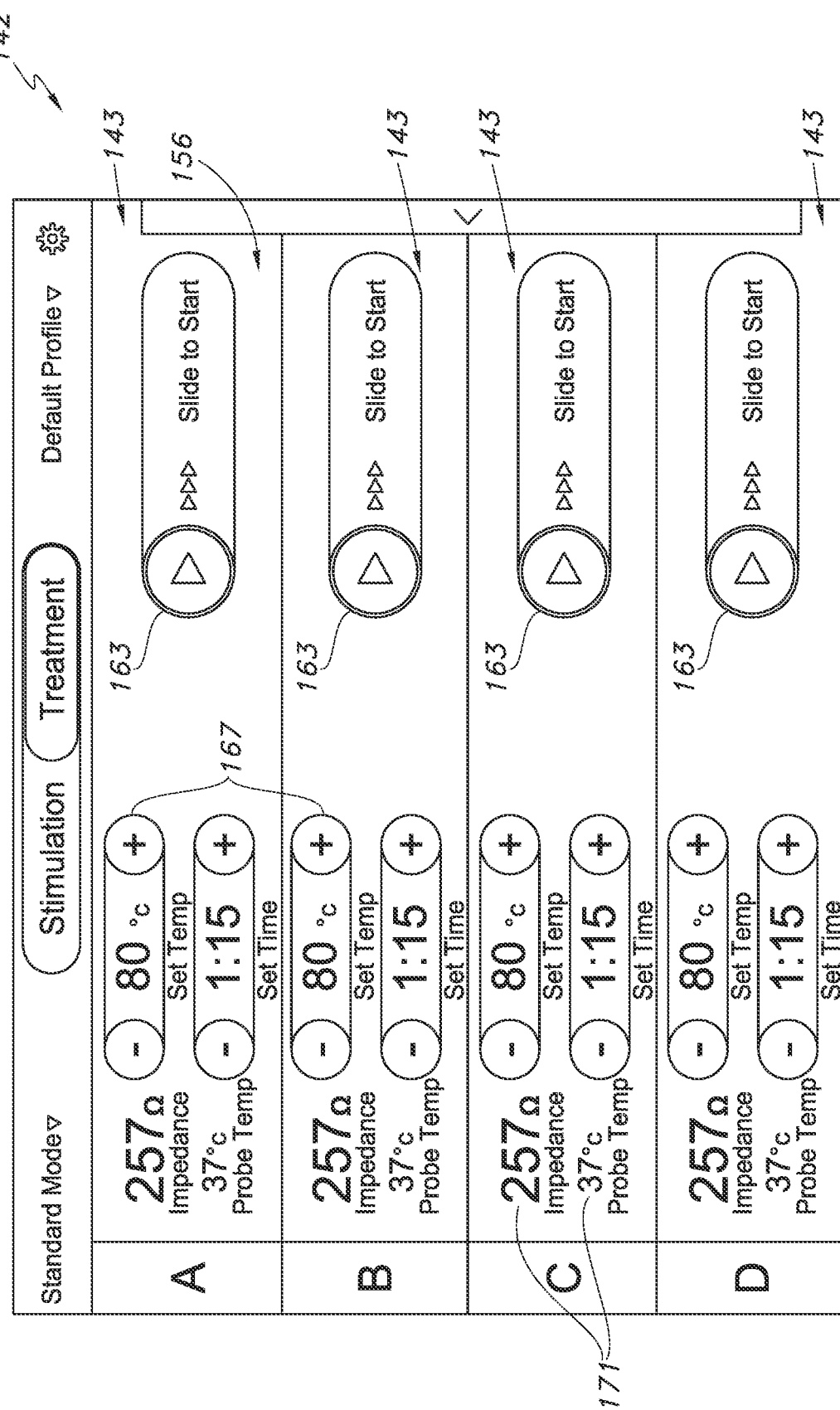
FIG. 4 illustrates a representation of one embodiment of a user interface of a controller of the probe assembly, particularly illustrating a plurality of dynamically sized channel control regions, according to some embodiments.

As shown in FIG. 4, the user can control the probes 107 individually via a plurality of respective channel control regions 143 displayed within the user interface 142. The user interface 142 can enable individual control of the probes 107 by incorporating a "swim lane" concept for each channel A, B, C, D, etc. As used herein, the "swim lane" generally refers to the idea of having respective channel control regions 143 associated with the probes 107. Various control objects can be provided within each respective channel control region 143 that allow the user to control aspects of the respective treatment procedures performed with the probes 107. One or more of the channel control regions 143 can include at least one of a start button, a restart button, a reset button, a stop button, or an independent sliding bar 163 that, upon engagement or selection by the user, is configured to start a treatment procedure for the selected probe 107 from the plurality of probes 107. In several embodiments, each of the channel control regions 143 may also include one or more individual parameter control buttons 167 for allowing the user to control aspects of the treatment procedures, for example, by modifying one or more of the operating parameters.

The respective channel control regions 143 can display one or more real-time operating parameters 171 of the treatment procedure. For example, as shown, the real-time operating parameters 171 may include an actual temperature, an impedance, an actual time, a run time, a power output of the associated energy delivery device 192, a threshold temperature, or combinations thereof.

Figure 5C:
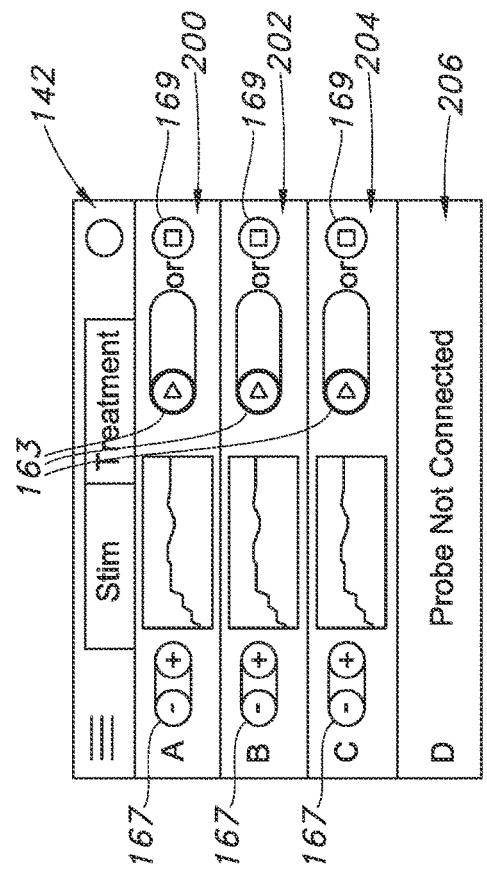
FIGS. 5A through 5C illustrate various embodiments of a user interface of a controller of the probe assembly, particularly illustrating various configurations of the plurality of dynamically sized channel control regions, according to some embodiments.
Figure 5B:
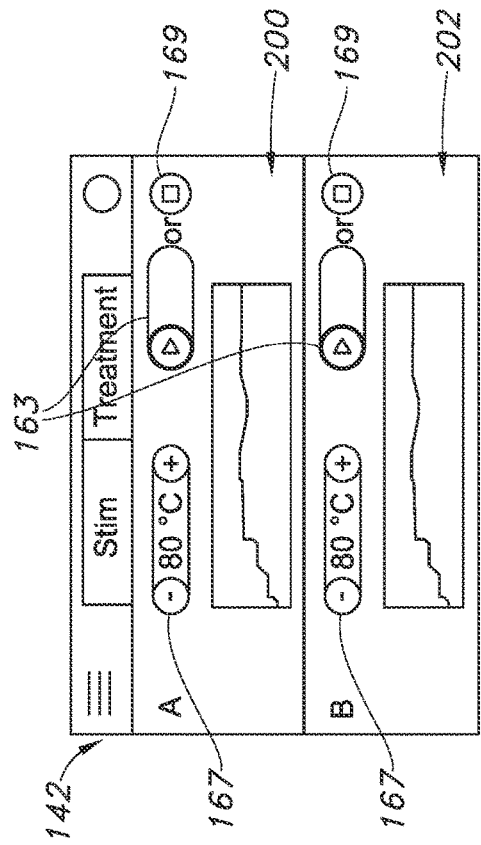
Figure 5A:
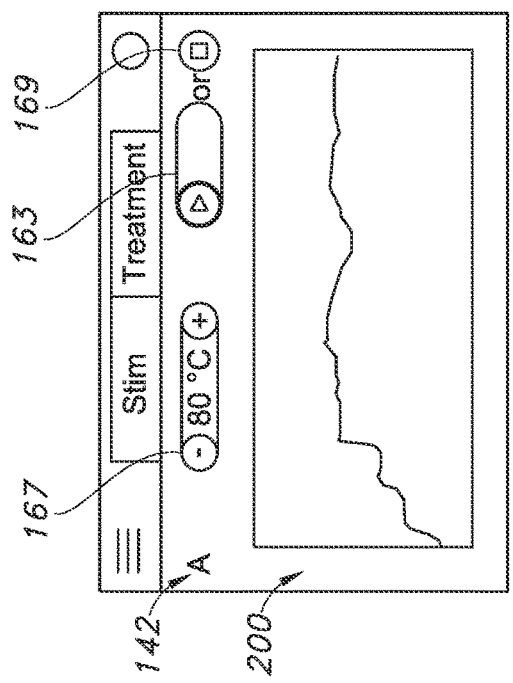

Referring to FIGS. 5A through 5C, in some embodiments, the controller 103 can be configured to dynamically size one or more channel control regions based at least in part on a number of the plurality of probes 107 that are communicatively coupled to the controller 103. The channel control regions 200, 202, 204 described with reference to FIGS. 5A through 5C may generally correspond with the channel control regions 143 described above with reference to FIG. 4. Referring to FIG. 5A, when a single probe 107 is communicatively coupled to the controller 103, a single, first channel control region 200 may be displayed in the user interface 142. Referring to FIG. 5B, when two probes 107 are communicatively coupled to the controller 103, the first channel control region 200 may be re-sized such that a second channel control region 202 may also be displayed in the user interface 142. For example, a size (e.g., height) of the first channel control region 200 may be reduced such the second channel control region 202 may be displayed. For example, the second control region 202 may have a height that is approximately equal to the height of the first channel control region.

Similarly, referring to FIG. 5C, when three probes 107 are communicatively coupled to the controller 103, the first and second channel control regions 200, 202 may be dynamically re-sized smaller such that a third channel control regions 204 may be displayed. The channel control regions 200, 202, 204 may be configured to display information associated with the each probe 107 corresponding with the respective channel control region 200, 202, 204.

In some embodiments, one or more notification regions 206 may be displayed that indicate an absence of an expected probe 107. For example, if the controller 103 has been initially configured, or set up, to perform a treatment procedure using four probes 107, yet only three probes 107 are connected, the controller 103 may provide the notification region 206 to alert the operator that the additional probe 107 has not yet been connected or is otherwise exhibiting connectivity issues.

The controller 103 may dynamically re-size the channel control regions 143 for example, in response to probes 107 being connected and/or disconnected from the controller 103. For example, if a single probe 107 is communicatively coupled to a controller 103, the controller 103 may initially display a single control region 143, for example as illustrated in FIG. 5A. If a second probe 107 is then communicatively coupled to the controller 103, the controller 103 may dynamically re-size the existing control region 200 to provide space for the second channel control region 202, for example as described above with reference to FIG. 5B. If a third probe 107 is then communicatively coupled to the controller 103, the controller 103 may dynamically re-size the existing first and second control regions 200, 202 and display the third channel control region 204, and, optionally, the notification region 206, for example as described above with reference to FIG. 5C.

The controller 103 may be configured to detect a user touch action directed to a user-selected channel control region of the plurality of dynamically sized channel control regions 202, 204, 206 of the user interface 142. When the user touch action is detected, the controller 103 may be configured to perform a control action associated with the probe 107 that corresponds with the user-selected channel control region of the plurality of dynamically sized channel control regions 200, 202, 204.

As an example, each of the channel control regions 143 may include one or more respective virtual control objects (e.g., independent sliding bars 163, individual parameter control buttons 167, and/or individual stop buttons 169), for example as illustrated in FIGS. 5A through 5C. The user can start, re-start, stop, and/or reset the treatment procedure by touching one or more of the virtual control objects. The user can adjust individual parameters (e.g., a duration time, a target temperature, stimulation, or treatment waveform, etc.) associated with performance of the treatment procedure of the corresponding probe 107.

It should be understood that displaying the control objects is not necessarily required. As another example, in some embodiments, at least one of the dynamically sized channel control regions 200, 202, 204 may be free of virtual control objects and responsive to user input. As an example, the user can touch one of the dynamically sized channel control regions 200, 202, 204 to cause the controller 103 to display a control dialog box (e.g., within the user-selected control region or superimposed over more than one of the regions). The control dialog box can include various virtual control objects for performing control actions (e.g., starting, stopping, and/or adjusting) with respect to the treatment procedure of the corresponding probe 107.

Figure 6:
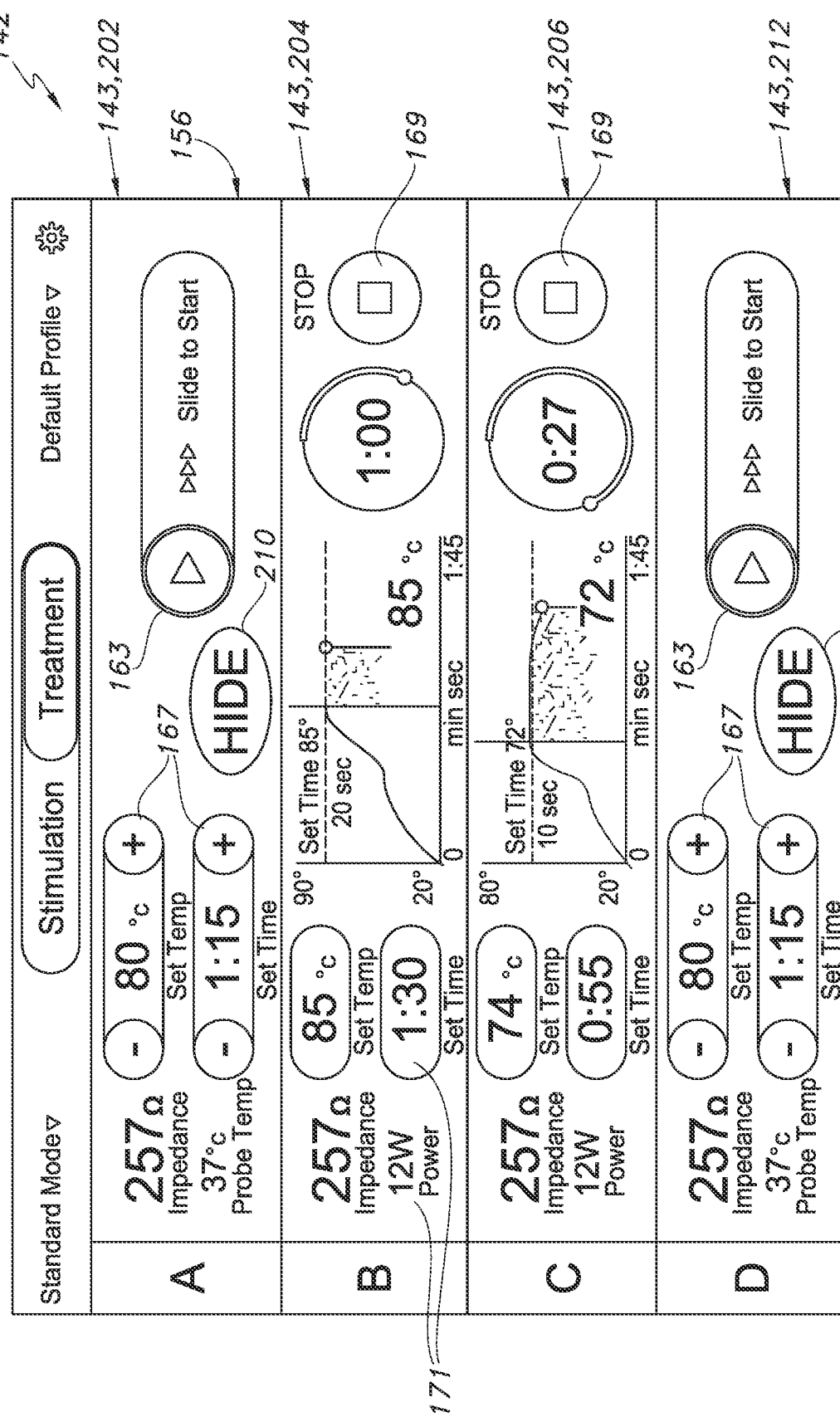
FIG. 6 illustrates a representation of another embodiment of a user interface, particularly illustrating the user interface with certain treatment procedures of selective probes initiated, according to some embodiments.

Referring to FIG. 6, in some embodiments, the controller 103 can selectively hide one or more of the dynamically sized channel control regions 143. For example, respective "hide" buttons 210 can be displayed within one or more of the dynamically sized channel control regions 143. The user can touch a "hide" button 210 of one of the dynamically sized channel control regions 143 to request that the channel control region 143 be hidden from view. In response, the controller 103 can be configured to resize the other dynamically sized channel control regions 143. This may provide the user with greater access to the control objects of the remaining control regions 143. As an example, in some embodiments, the number of dynamic control objects displayed within each channel control region 143 may be increased in response to the number of channel control regions 143 being reduced as more space is thereby provided for the remaining channel control regions 143.

In some embodiments, channel control regions that correspond with "inactive" probes 107 can display "hide" buttons 210. Channel control regions that correspond with "active" probes, in contrast, may display other virtual control buttons, such as the stop button 169. In this example, the second and third channel control regions 204, 206 indicate that the corresponding probes 107 are actively performing treatment procedures. The first channel control region 202 and a fourth channel control region 212 indicate that their corresponding probes 107 are inactive. The controller 103 may be configured to display the "hide" buttons 210 in the "inactive" channel control regions 202, 212 such that the user can selectively hide the "inactive" channel control regions 202, 212.

In some embodiments, the controller 103 can be configured to resize the plurality of dynamically sized channel control regions 143 in response to completed performance of a treatment procedure of at least one of the plurality of probes 107. As an example, when the treatment procedure associated with the third channel control region 206 is completed, the controller 103 can automatically resize the remaining channel control regions 202, 204, 208 to be larger. The third channel control region 206 can be hidden or re-sized to be smaller.

Figure 7:
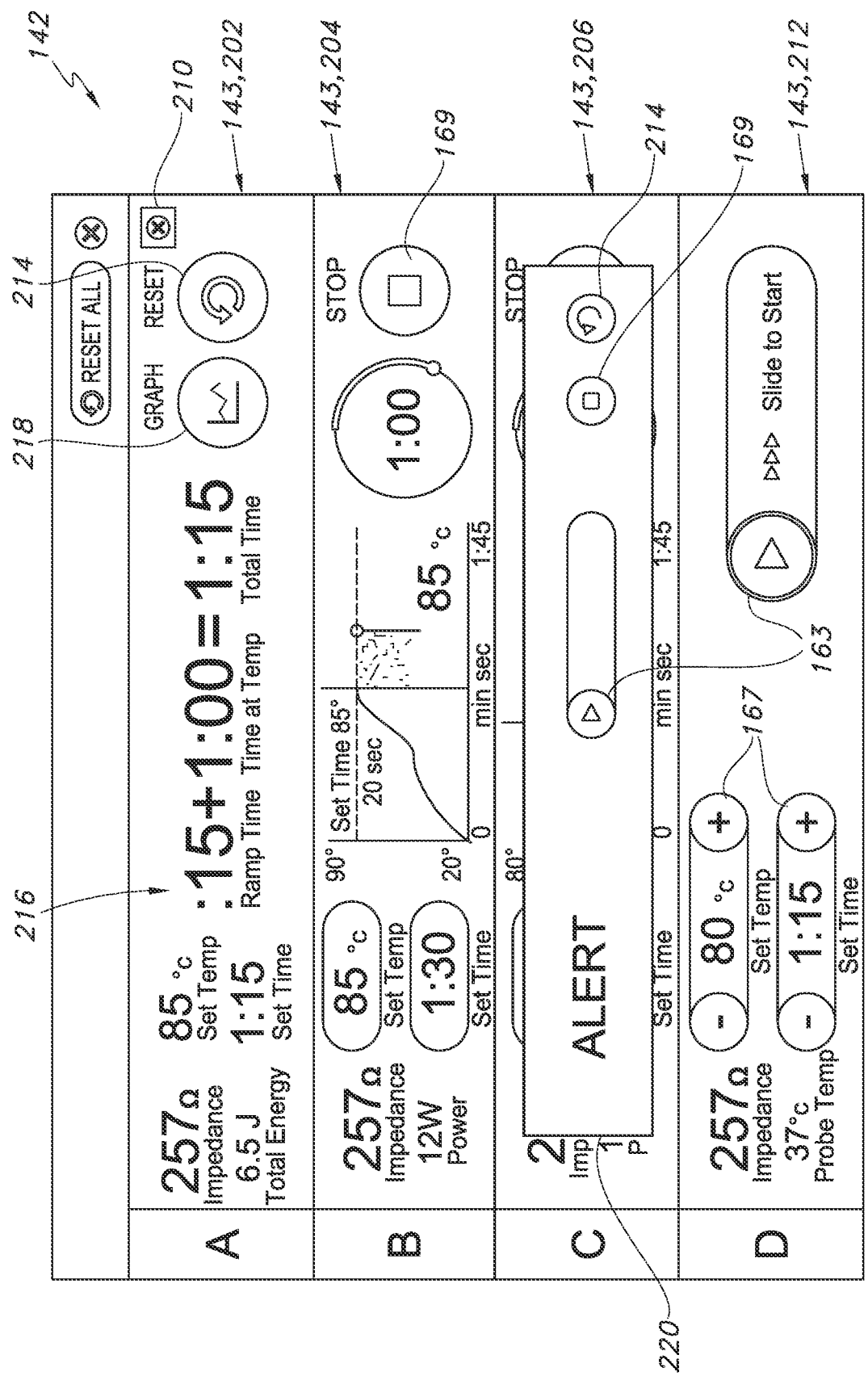
FIG. 7 illustrates a representation of another embodiment of a user interface, particularly illustrating the user interface including channel control regions in a variety of conditions, according to some embodiments.

Referring to FIG. 7, in some embodiments, the controller 103 may be configured to facilitate individual control the respective probes 107 and associated treatment procedures. For example, the controller 103 may be configured to provide the user with the ability to restart or reset a treatment procedure that has been completed. The controller 103 may additionally display information 216 about the completed treatment procedure and/or a button 218 for requesting additional information about the completed procedure (e.g., a graph or plot of one or more of operating parameters against time during the procedure). A "hide" button 210 may be displayed within the channel control region 143 once the treatment procedure has been completed, for example as described above with reference to FIG. 6. The user may be able to hide or reduce the size of the completed channel control region 143 using the "hide" button 210, for example as described above with reference to FIG. 6.

The controller 103 may also be configured to provide the user with the ability to reset and/or restart individual treatment procedures. For example, if a probe 107 experiences unsatisfactory operating conditions, the controller 103 may be configured to automatically terminate the associated treatment procedure or provide an alert to the user recommending that the treatment procedure be terminated. Such unsatisfactory operating conditions may be defined based on a comparison between an operating parameter and an associated threshold or target value. For example, the controller 103 may be configured to detect when an operating parameter (e.g., an actual temperature, impedance, power output, etc.) has exceeded a threshold associated with the operating parameter, for example as described above with reference to FIG. 3. Depending on the severity of the problem, the controller 103 may automatically stop the treatment procedure or may provide the alert to the user.

For example, the controller 103 may be configured to display the status notification 220, or alert, when the actual temperature of tissue near the probe 107 (e.g., as measured by the temperature sensing elements 402, 404) exceeds a temperature threshold range with respect to a target temperature for the treatment procedure. The status notification 220 (e.g., a superimposed window) may be displayed that describes a status of one of the dynamically sized channel control regions 143. The status notification 220 can be displayed within the dynamically sized channel control region 143 that corresponds with the probe 107 performing the treatment procedure that has the unsatisfactory operating condition. The status notification 220 can include information describing the unsatisfactory condition with the treatment procedure. Such information can be useful for troubleshooting the issue. The status notification 220 can also include a variety of virtual control objects, such as a reset button 214, stop button 169, and/or sliding bar 163. If the controller 103 has automatically stopped the treatment procedure, the user can troubleshoot the issue (e.g., based on the information provided). The user can decide whether to reset or restart the treatment procedure using the reset button 213 or slider bar 163, for example. If the treatment procedure has not been automatically stopped, the user can evaluate the information about the unsatisfactory condition, troubleshoot the issue (e.g., based on the information provided), and decide whether to stop the treatment procedure using the stop button 169.

It should be understood that during the above-described stopping and starting of an individual treatment procedure, the controller 103 may be configured to continue controlling and/or monitoring the remaining treatment procedures. As shown in FIG. 7, in one example, each treatment procedure may be in a different state: completed, actively being performed, stopped with a status notification 220, and not yet initiated.

Figure 8:
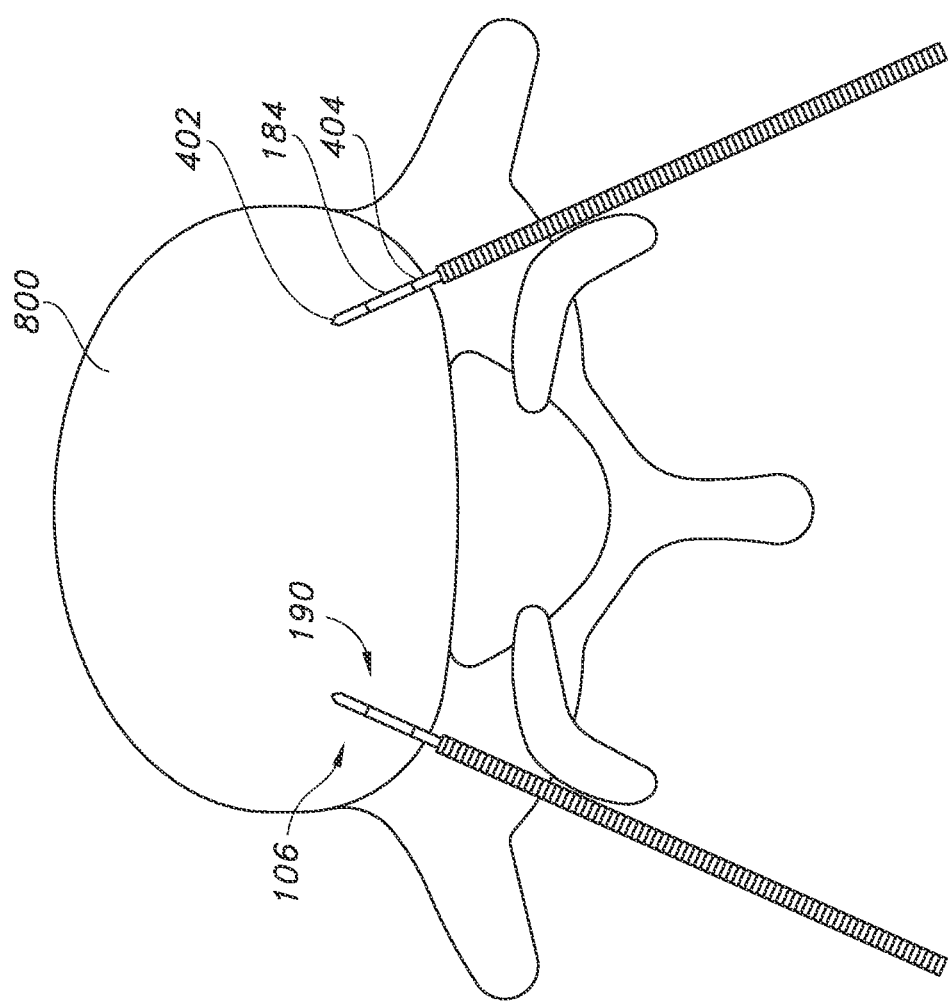
FIG. 8 illustrates two probes placed within an intervertebral disc, according to some embodiments.

In one embodiment, the plurality of probes 107 may be operated in a bipolar mode. For example, FIG. 8 illustrates one embodiment of two probes 107, wherein the distal tip regions 190 thereof are located within an intervertebral disc 800. In such embodiments, electrical energy is delivered to the probes 107 and this energy is preferentially concentrated therebetween through a region of tissue to be treated (i.e., an area of the intervertebral disc 800). The region of tissue to be treated is thus heated by the energy concentrated between the probes 107. In other embodiments, the probes 107 may be operated in a monopolar mode, in which case an additional grounding pad is required on the surface of a body of a patient, as is known in the art. Any combination of bipolar and monopolar procedures may also be used. It should also be understood that the system may include more than two probe assemblies. For example, in some embodiments, three probe assemblies may be used and the probe assemblies may be operated in a triphasic mode, whereby the phase of the current being supplied differs for each probe assembly.

Figure 9A:
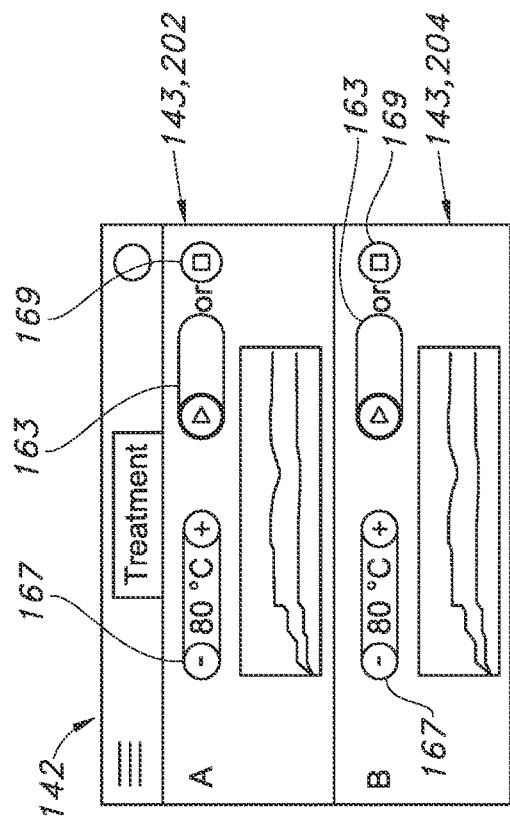
FIG. 9A through 9D illustrate various embodiments of a user interface, particularly illustrating a variety of configurations of the dynamically sized channel control regions, according to some embodiments.
Figure 9B:
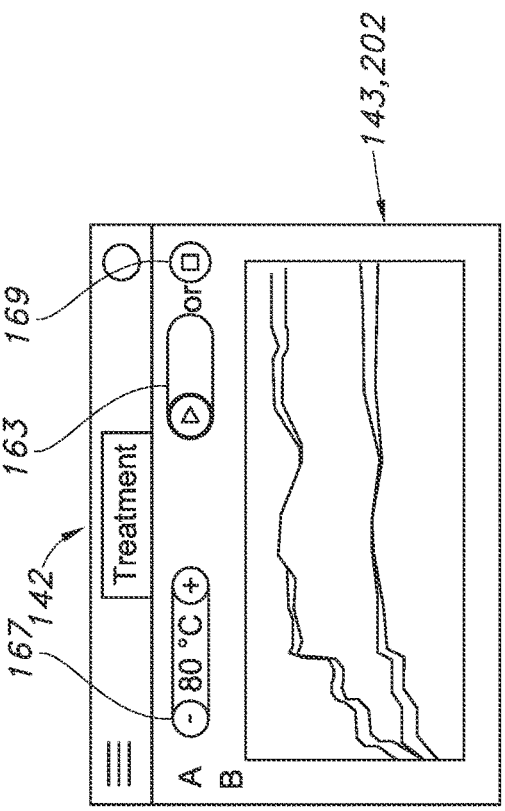
Figure 9C:
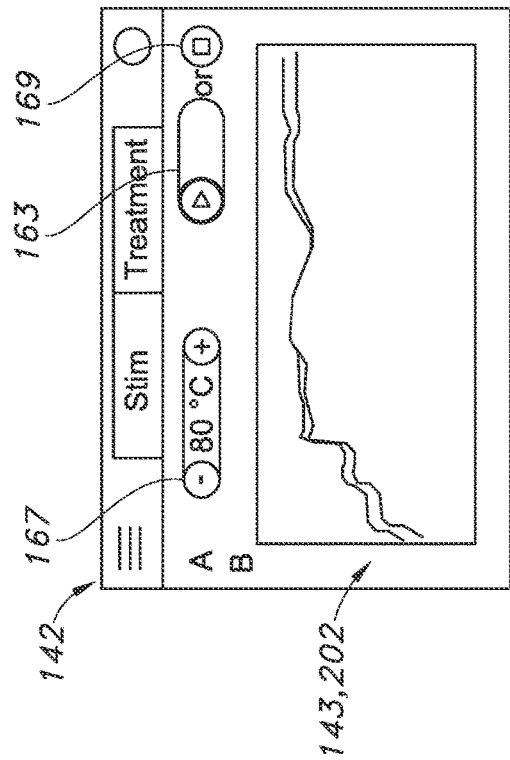
Figure 9D:
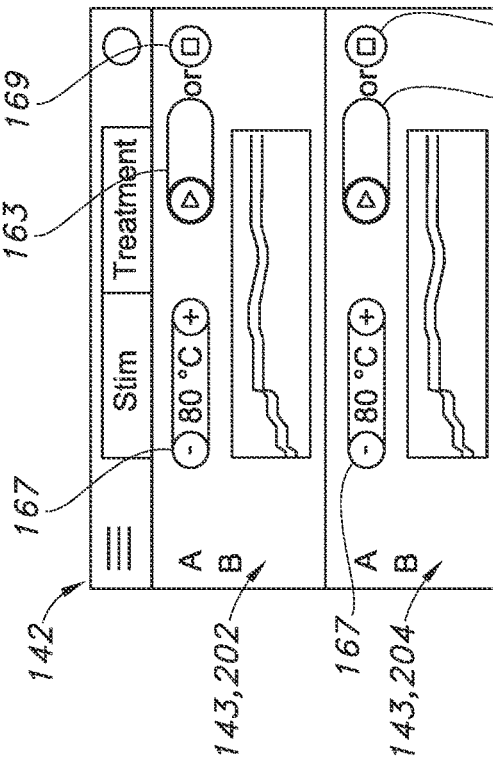

Referring to FIG. 9A through 9D, the controller 103 may be configured to display information about multiple probes 107 within a single dynamically sized channel control region 134 in a variety of suitable configurations and operation modes. As shown in FIG. 9A, respective signals from a pair of probes 107 may be displayed within the same channel region 134. Referring to FIG. 9B, first and second channel regions 202, 204 may be provided for respective probes 107 that are each operated in a monopolar mode. Referring to FIG. 9C, first and second channel regions 202, 204 may be provided for respective pairs of probes 107. Referring to FIG. 9D, in some embodiments, the controller 103 may provide a single control region 143 for a plurality of probes 107 that are operated in a bipolar mode. It should be understood that a variety of other variations and combinations are possible within the scope of this disclosure.

Figure 10:
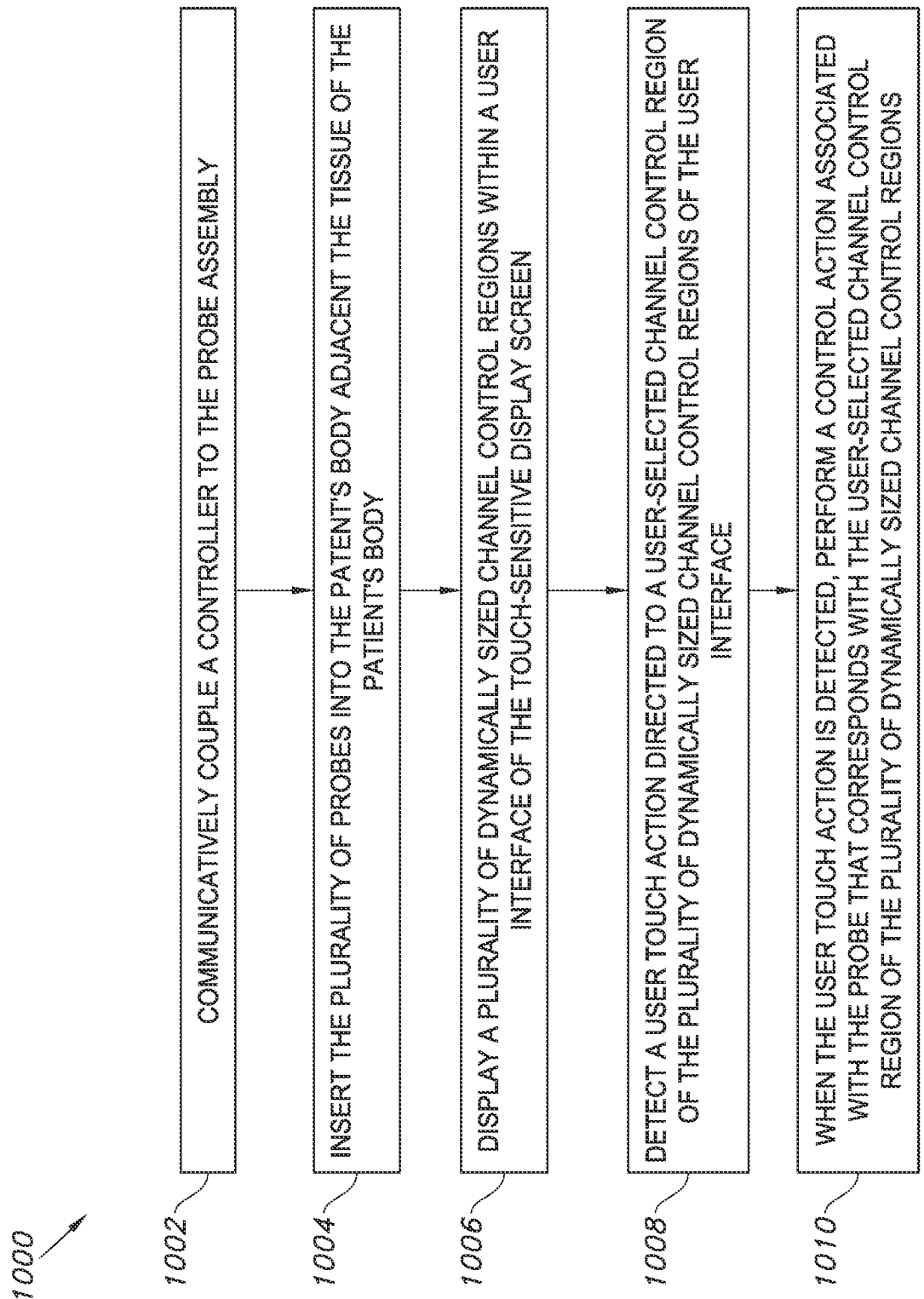
FIG. 10 illustrates a flow diagram of one embodiment of a method of treating tissue of a patient's body, according to some embodiments.

Referring to FIG. 10, a block diagram of one embodiment of a method 1000 of treating tissue of a patient's body, such as an intervertebral disc 800, using the probe assemblies described herein is illustrated. The method 1000 may include, at (1002), communicatively coupling the controller 103 to the probe assembly 106. Further, the controller 103 can be communicatively coupled to the display screen 123, which can be a touch-sensitive display that can display the user interface 142.

The method 1000 can include, at (1004), inserting the plurality of probes 107 into the patient's body adjacent the tissue of the patient's body to be treated. For example, in one embodiment, with a patient lying on a radiolucent table, fluoroscopic guidance may be used to percutaneously insert an introducer with a stylet to access the posterior of an intervertebral disc. In addition to fluoroscopy, other aids, including but not limited to impedance monitoring and tactile feedback, may be used to assist a user to position the introducer or probes 107 within the patient's body. The use of impedance monitoring has been described herein, whereby a user may distinguish between tissues by monitoring impedance as a device is inserted into the patient's body. With respect to tactile feedback, different tissues may offer different amounts of physical resistance to an insertional force. This allows a user to distinguish between different tissues by feeling the force required to insert a device through a given tissue.

At (1006), the method 1000 may include displaying a plurality of dynamically sized channel control regions within a user interface of a touch-sensitive display screen, for example, as described above with reference to FIGS. 4 through 9D. Each of the plurality of dynamically sized channel control regions may correspond with one of the plurality of probes. The plurality of dynamically sized channel control regions may be sized based at least in part on a number of the plurality of probes. As an example, each dynamically sized channel control region may correspond with a single probe. As discussed above, in some embodiments, multiple probes may correspond with a single dynamically sized channel control region.

The method 1000 may include resizing the plurality of dynamically sized channel control regions in response to an additional probe being communicatively coupled with the controller, for example as described above with reference to FIGS. 5A through 5C. In some embodiments, the method may include resizing the plurality of dynamically sized channel control regions in response to the user touch action when the user touch action requests that the user-selected channel control region be hidden from the user interface, for example as described above with reference to FIGS. 6 and 7. In some embodiments, the method may include resizing the plurality of dynamically sized channel control regions in response to completed performance of a treatment procedure of at least one of the plurality of probes, for example as described above with reference to FIG. 7.

The method 1000 may include, at (1008), detecting a user touch action directed to a user-selected channel control region of the plurality of dynamically sized channel control regions of the user interface. As an example, a virtual control object may be displayed within at least one of the plurality of dynamically sized channel control regions. The user touch action may be directed to the virtual control object of the user-selected channel control region. The virtual control object may include at least one of a start button, a restart button, a reset button, a stop button, or an individual parameter control button, for example as described above with reference to FIGS. 4 through 9D. The virtual control object may include a slider bar, and the method 1000 may further include initiating, resetting, or restarting a treatment procedure with the at least one probe that corresponds with the user-selected channel control region. As an example, in some embodiments, the method 1000 may include monitoring a status of a treatment procedure associated with at least one of the plurality of probes and displaying a status notification indicative of the status within the dynamically sized channel control region that corresponds with the at least one of the plurality of probes, for example as described above with reference to FIG. 7.

During the procedure, a treatment protocol such as the cooling supplied to the probes 107 and/or the power transmitted to the probes 107 may be adjusted and/or controlled to maintain a desirable treatment area shape, size, and uniformity. The controller 103 may be configured to control one or more aspects of the various treatment procedures based on one or more target parameters and/or one or more sensed values, for example using a control loop as described above with reference to FIGS. 1A and 3.

The method may include, at (1010), performing a control action associated with the probe that corresponds with the user-selected channel control region of the plurality of dynamically sized channel control regions when the user touch action is detected. The control action may include starting, stopping, re-starting, and/or resetting the treatment procedure of the probe that corresponds with the user-selected channel control region. As an example, the virtual control object may include an individual parameter control button (e.g., a temperature setting button or an individual duration time button). Performing the control action may include adjusting an individual parameter setting (e.g., a temperature setting, an impedance setting, an individual duration time, or a power output setting) associated with the treatment procedure (e.g., of the at least one probe that corresponds with the user-selected channel control region). Operation of the controller 103 may be adjusted accordingly. A cooling rate, energy delivery rate, etc., may be adjusted according to one or more control loops, based on a target parameter (e.g., temperature, impedance, etc.) for example as described above with reference to FIGS. 1A and 3.

A system of the present invention may be used in various medical procedures where usage of an energy delivery device may prove beneficial. Specifically, the system of the present invention is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

Using liquid-cooled probes 107 with an appropriate feedback control system as described herein also contributes to the uniformity of the treatment. The cooling distal tip regions 190 of the probes 107 helps to prevent excessively high temperatures in these regions which may lead to tissue adhering to the probes 107 as well as an increase in the impedance of tissue surrounding the distal tip regions 190 of the probes 107. Thus, by cooling the distal tip regions 190 of the probes 107, higher power can be delivered to tissue with a minimal risk of tissue charring at or immediately surrounding the distal tip regions 190. Delivering higher power to energy delivery devices 192 allows tissue further away from the energy delivery devices 192 to reach a temperature high enough to create a lesion and thus the lesion will not be limited to a region of tissue immediately surrounding the energy delivery devices 192 but will rather extend preferentially from a distal tip region 190 of one probe assembly 106 to the other.

It should be noted that the term radiopaque marker as used herein denotes any addition or reduction of material that increases or reduces the radiopacity of the device. Furthermore, the terms probe assembly, introducer, stylet etc. are not intended to be limiting and denote any medical and surgical tools that can be used to perform similar functions to those described. In addition, the invention is not limited to be used in the clinical applications disclosed herein, and other medical and surgical procedures wherein a device of the present invention would be useful are included within the scope of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An ablation system comprising:
    one or more probes for delivering radiofrequency (RF) energy to a patient;
    a touch-sensitive display screen; and
    a controller communicatively coupled to each of the one or more probes and the touch- sensitive display screen, the controller comprising a processor and memory having instructions stored thereon that, when executed by the processor, cause the processor to perform operations comprising:
        displaying, on the touch-sensitive display screen and responsive to a first probe of the one or more probes being coupled to the controller, a user interface comprising a first channel control region corresponding to the first probe; and
        responsive to a second probe of the one or more probes being coupled to the controller, modifying the user interface by: i) adding a second channel control region corresponding to the second probe to the user interface, and ii) dynamically resizing and repositioning the first channel control region to accommodate the second channel control region, wherein:
            each of the first channel control region and the second channel control region include one or more graphical elements for controlling an operation of a corresponding one of the first probe and the second probe, and
            each of the first channel control region and the second channel control region indicate real-time operating parameters associated with the operation of the corresponding one of the first probe and the second probe.

2. The system of claim 1, the operations further comprising:
    receiving a user input via the touch-sensitive display screen, the user input comprising a selection of an icon on the user interface that causes one of the first channel control region or the second channel control region to be hidden; and
    modifying the user interface by i) hiding the selected one of the first channel control region or the second channel control region from the user interface, and ii) dynamically resizing and repositioning a non-selected one of the first channel control region or the second channel control region to fill the user interface.

3. The system of claim 1, the operations further comprising:
    determining that a treatment procedure performed by one of the first probe or the second probe has completed; and
    modifying the user interface by i) removing, from the user interface, one of the first channel control region or the second channel control region corresponding to the first probe or the second probe which has completed the treatment procedure, and ii) dynamically resizing and repositioning a remaining one of the first channel control region or the second channel control region to fill the user interface.

4. The system of claim 1, the operations further comprising:
    monitoring a status of a treatment procedure associated with at least one of the first probe or the second probe; and
    displaying, via the user interface, a notification indicating the status of the treatment procedure within a corresponding one of the first channel control region or the second channel control region.

5. The system of claim 1, the operations further comprising:
    responsive to one of the first probe or the second probe being disconnected from the controller, modifying the user interface by: i) removing a corresponding one of the first channel control region or the second channel control region from the user interface, and ii) dynamically resizing and repositioning a remaining one of the first channel control region or the second channel control region to fill the user interface.

6. The system of claim 1, the operations further comprising:
    responsive to one of the first probe or the second probe completing a treatment procedure, displaying, within a corresponding one of the first channel control region or the second channel control region, a summary of operating parameters of the first probe or the second probe over a time period of the treatment procedure.

7. The system of claim 1, wherein the one or more graphical elements include one or more of a start button or a sliding bar for initiating a treatment procedure, a restart button for restarting the treatment procedure, a reset button for resetting treatment parameters associated with a correspond one of the first probe or the second probe, or a stop button for stopping the treatment procedure.

8. The system of claim 1, wherein the one or more graphical elements include one or more operating parameter controls icons, the operations further comprising:
   receiving a user input to the one or more graphical elements via the touch-sensitive display screen, the user input comprising an adjustment to at least one operating parameter of the first probe or the second probe; and
   adjusting the at least one operating parameter prior to or during a treatment procedure performed by the first probe or the second probe.

9. The system of claim 1, wherein each of the one or more probes comprise:
   a handle;
   a hollow elongate shaft extending distally from the handle;
   an RF energy delivery device positioned at a distal end of the hollow elongate shaft opposite the handle, the RF energy delivery device configured to deliver the RF energy to the patient; and
   one or more cooling fluid supply tubes extending along a portion of, and internally to, the hollow elongate shaft, wherein the one or more cooling fluid supply tubes are configured to transfer a cooling fluid from a pump, to the distal end of the hollow elongate shaft, and back to the pump.

10. A method of dynamically modifying a user interface for operating an ablation system, the method comprising:
    displaying the user interface on a touch-sensitive display screen of the ablation system;
    modifying the user interface to include a first channel control region responsive to a first ablation probe being electrically coupled to the ablation system, wherein the first channel control region includes a first set of graphical elements for controlling an operation of the first ablation probe, and wherein the first channel control region indicates real-time operating parameters associated with the operation of the first ablation probe;
    detecting that a second ablation probe is electrically coupled to the ablation system; and
    modifying the user interface to include a second channel control region responsive to the detection of the second probe, wherein modifying the user interface to include the second channel control region comprises dynamically resizing and repositioning the first channel control region to accommodate the second channel control region, the second channel control region including a second set of graphical elements for controlling an operation of the second ablation probe and the second channel control region indicating real-time operating parameters associated with the operation of the second ablation probe.

11. The method of claim 10, further comprising:
    receiving a user input via the touch-sensitive display screen, the user input comprising a selection of an icon on the user interface that causes one of the first channel control region or the second channel control region to be hidden; and
    modifying the user interface by: i) hiding the selected one of the first channel control region or the second channel control region from the user interface, and ii) dynamically resizing and repositioning a non-selected one of the first channel control region or the second channel control region to fill the user interface.

12. The method of claim 10, further comprising:
    determining that a treatment procedure performed by one of the first ablation probe or the second ablation probe has completed; and
    modifying the user interface by: i) removing, from the user interface, one of the first channel control region or the second channel control region corresponding to the first ablation probe or the second ablation probe which has completed the treatment procedure, and ii) dynamically resizing and repositioning a remaining one of the first channel control region or the second channel control region to fill the user interface.

13. The method of claim 10, further comprising:
    monitoring a status of a treatment procedure associated with at least one of the first ablation probe or the second ablation probe; and
    displaying, via the user interface, a notification indicating the status of the treatment procedure within a corresponding one of the first channel control region or the second channel control region.

14. The method of claim 10, further comprising:
    detecting that one of the first ablation probe or the second ablation probe is disconnected from the ablation system; and
    modifying the user interface responsive to detecting that one of the first ablation probe or the second ablation probe is disconnected by: i) removing a corresponding one of the first channel control region or the second channel control region from the user interface, and ii) dynamically resizing and repositioning a remaining one of the first channel control region or the second channel control region to fill the user interface.

15. The method of claim 10, further comprising:
    determining that one of the first ablation probe or the second ablation probe has completed a treatment procedure; and
    responsive to determining that one of the first probe or the second probe has completed the treatment procedure, displaying, within a corresponding one of the first channel control region or the second channel control region, a summary of operating parameters of the first ablation probe or the second ablation probe over a time period of the treatment procedure.

16. The method of claim 10, wherein the first set of graphical elements and the second set of graphical elements include one or more of a start button or a sliding bar for initiating a treatment procedure, a restart button for restarting the treatment procedure, a reset button for resetting treatment parameters associated with a correspond one of the first probe or the second probe, or a stop button for stopping the treatment procedure.

17. The method of claim 10, wherein the first set of graphical elements and the first set of graphical elements each include one or more operating parameter controls icons, the method further comprising:
    receiving a user input to the one or more operating parameter controls icons via the touch-sensitive display screen, the user input comprising an adjustment to an operating parameter of one of the first ablation probe or the second ablation probe; and adjusting the operating parameter prior to, or during, a treatment procedure performed by the first ablation probe or the second ablation probe.

18. A device for applying radiofrequency (RF) energy to a patient, the device comprising:

a touch-sensitive display screen;

a processor; and memory having instructions stored thereon that, when executed by the processor, cause the device to:

display, on the touch-sensitive display screen, a user interface for controlling a plurality of probes for applying the RF energy, wherein the plurality of probes are selectively connected to the device, and wherein the user interface comprises a channel control region for each of the plurality of probes that are actively connected to the device;

detect whether at least one probe of the plurality of probes is disconnected from the device or whether an additional probe is connected to the device; and modify the user interface by:

removing, from the user interface and responsive to detecting that at least one probe of the plurality of probes is disconnected from the device, the channel control region corresponding to the disconnected probe, and dynamically resizing and repositioning the remaining channel control regions to fill the user interface; or adding, from the user interface and responsive to detecting that the additional probe is connected to the device, a new channel control region corresponding to the additional probe, and dynamically resizing and repositioning the original channel control regions to accommodate the new channel control region;

wherein each of the channel control regions include graphical elements for controlling an operation of a corresponding probe of the plurality of probes, and wherein each of the channel control regions indicate real-time operating parameters of the corresponding probe of the plurality of probes.

19. The device of claim 18, wherein the graphical elements include one or more of a start button or a sliding bar for initiating a treatment procedure, a restart button for restarting the treatment procedure, a reset button for resetting treatment parameters associated with a correspond one of the plurality of probes, or a stop button for stopping the treatment procedure.

20. The device of claim 18, wherein each of the plurality of probes comprise:

a handle;

a hollow elongate shaft extending distally from the handle;

an RF energy delivery device positioned at a distal end of the hollow elongate shaft opposite the handle, the RF energy delivery device configured to deliver the RF energy to the patient; and one or more cooling fluid supply tubes extending along a portion of, and internally to, the hollow elongate shaft, wherein the one or more cooling fluid supply tubes are configured to transfer a cooling fluid from a pump, to the distal end of the hollow elongate shaft, and back to the pump.

* * * * *